United States Patent
Williams et al.

(10) Patent No.: US 11,612,400 B2
(45) Date of Patent: Mar. 28, 2023

(54) TROCAR ASSEMBLY WITH BEARING ASSEMBLY FOR LOAD SHARING

(71) Applicant: Covidien LP, Mansfield, MA (US)

(72) Inventors: Justin Williams, Southbury, CT (US); Christopher W. Kaswer, Avon, CT (US)

(73) Assignee: COVIDIEN LP, Mansfield, MA (US)

( * ) Notice: Subject to any disclaimer, the term of this patent is extended or adjusted under 35 U.S.C. 154(b) by 122 days.

(21) Appl. No.: 17/328,120

(22) Filed: May 24, 2021

(65) Prior Publication Data
US 2022/0370072 A1  Nov. 24, 2022

(51) Int. Cl.
*A61B 17/115* (2006.01)
*A61B 17/34* (2006.01)

(52) U.S. Cl.
CPC ...... *A61B 17/1155* (2013.01); *A61B 17/3403* (2013.01); *A61B 2017/3407* (2013.01)

(58) Field of Classification Search
CPC .......... A61B 17/3404; A61B 17/1155
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

International Search Report and Written Opinion issued in corresponding International Application No. PCT/IB2022/054697 dated Aug. 25, 2022, 12 pages.

(Continued)

*Primary Examiner* — Nathaniel C Chukwurah
(74) *Attorney, Agent, or Firm* — Carter, DeLuca & Farrell, LLP

(57) ABSTRACT

A trocar assembly for releasable engagement with an adapter assembly of a surgical stapling instrument includes a bearing assembly for distributing the axial load experienced by a drive member during tissue stapling. The bearing assembly is disposed within a housing between a flange of the housing and a flange of a drive member. The bearing assembly is configured to rotatably support the drive member and includes a thrust bearing, a rigid member, and a compressible member disposed between the thrust bearing and the rigid member. The compressible member includes a first compressed condition having a first thickness during a clamping stroke of the surgical stapling instrument and a second compressed condition having a second thickness during a stapling stroke of the surgical stapling instrument. The second thickness is less than the first thickness.

20 Claims, 14 Drawing Sheets

(56) References Cited

U.S. PATENT DOCUMENTS

| | | |
|---|---|---|
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |

(56) References Cited

U.S. PATENT DOCUMENTS

| | | |
|---|---|---|
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |

(56) References Cited

U.S. PATENT DOCUMENTS

| | | |
|---|---|---|
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 3,002,795 A1 | 8/2011 | Beetel |
| 3,006,701 A1 | 8/2011 | Bilotti et al. |
| 3,006,889 A1 | 8/2011 | Adams et al. |
| 3,011,551 A1 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 3,038,046 A1 | 10/2011 | Smith et al. |
| 3,043,207 A1 | 10/2011 | Adams |
| 8,028,885 B2 | 10/2011 | Smith et al. |
| 3,066,167 A1 | 11/2011 | Measamer et al. |
| 3,066,169 A1 | 11/2011 | Viola |
| 3,070,035 A1 | 12/2011 | Holsten et al. |
| 3,070,037 A1 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |
| 9,364,229 B2 | 6/2016 | D'Agostino et al. |

(56) References Cited

U.S. PATENT DOCUMENTS

| | | |
|---|---|---|
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,226,254 B2 * | 3/2019 | Cabrera ............ A61B 17/1155 |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2014/0008413 A1 | 1/2014 | Williams |
| 2014/0046352 A1 | 2/2014 | Reboa et al. |
| 2014/0158747 A1 | 6/2014 | Measamer et al. |
| 2014/0284370 A1 | 9/2014 | Sahin |
| 2015/0083772 A1 | 3/2015 | Miller et al. |
| 2015/0173763 A1 | 6/2015 | Liu |

(56) References Cited

U.S. PATENT DOCUMENTS

| | | | |
|---|---|---|---|
| 2015/0209045 A1 | 7/2015 | Hodgkinson et al. | |
| 2017/0105735 A1* | 4/2017 | Williams | A61B 17/1155 |

FOREIGN PATENT DOCUMENTS

| | | |
|---|---|---|
| CN | 104039244 A | 9/2014 |
| CN | 104042288 A | 9/2014 |
| CN | 104367360 A | 2/2015 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1671597 A1 | 6/2006 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3023077 A1 | 5/2016 |
| EP | 3078335 A1 | 10/2016 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 02080781 A2 | 10/2002 |
| WO | 2004047654 A2 | 6/2004 |
| WO | 2008107918 A1 | 9/2008 |

OTHER PUBLICATIONS

Extended European Search Report from Appl. No. 14181908.6 dated May 26, 2015.

European Examination Report from Appl. No. 14181908.6 dated May 3, 2016.

* cited by examiner

TROCAR ASSEMBLY WITH BEARING ASSEMBLY FOR LOAD SHARING

FIELD

The disclosure relates to trocar assemblies for adapter assemblies of surgical stapling instruments. More particularly, the disclosure relates to adapter assemblies having a trocar assembly with a bearing assembly configured for load sharing during a stapling procedure.

BACKGROUND

Surgical stapling instruments for creating an anastomosis in tubular organs or vessels is known. These surgical stapling instruments may include an actuation assembly or handle, an adapter assembly supporting a circular loading unit, and an anvil assembly movable relative to the loading unit. The anvil assembly is releasably securable to a trocar member of a trocar assembly of the adapter assembly. The trocar member is advanceable and retractable relative to the circular loading unit to reposition the anvil assembly relative to the loading unit.

During a stapling procedure, the trocar member experiences a first, dynamic load during the clamping of tissue, and a second, static load during the stapling and/or cutting of tissue. The cutting of tissue may occur simultaneously with the stapling of tissue or as an additional operation. The static load experienced by the trocar member during the stapling of tissue is significantly greater than the dynamic load experienced by the trocar member during clamping of tissue. Thrust bearings are well suited to provide smooth, low friction rotation of a drive member during the reduced dynamic loading that occurs during clamping of tissue, however, limitations in size and space prevent a thrust bearing capable of handling the maximum, static loads during stapling and/or cutting of tissue.

Therefore, it would be beneficial to have a trocar assembly including a thrust bearing for accommodating the dynamic loading that occurs during clamping of tissue and a mechanism for distributing the increased static load during stapling and/or cutting of tissue.

SUMMARY

A trocar assembly for a surgical stapling instrument includes a housing, a trocar member, a drive member, and a bearing assembly. The housing includes a tubular body having a proximal portion and a distal portion, and a flange. The trocar member is slidably supported within the housing and is movable between a retracted position and an advanced position. The drive member is in operable engagement with the trocar member to cause longitudinal movement of the trocar member relative to the housing between the advanced position and the retracted position. The drive member also includes a flange. The bearing assembly is disposed within the housing between the flange of the housing and the flange of the drive member. The bearing assembly is configured to rotatably support the drive member and includes a thrust bearing, a rigid member, and a compressible member disposed between the thrust bearing and the rigid member. The compressible member includes a first compressed condition having a first thickness during a clamping stroke of the surgical stapling instrument and a second compressed condition having a second thickness during a stapling stroke of the surgical stapling instrument. The second thickness is less than the first thickness.

In certain aspects of the disclosure, the rigid member is spaced from the flange of the drive member during the clamping stroke of the surgical stapling instrument. The rigid member may be in engagement with the flange of the drive member during the stapling stroke of the surgical stapling instrument. The compressible member may include an uncompressed condition. The rigid member may be spaced from the flange of the drive member prior to the clamping stroke of the surgical stapling instrument. The compressible member may transition from the uncompressed condition to the first compressed condition as the trocar member moves from the advanced position to the retracted position. The rigid member may include a proximal annular portion and a distal annular portion. The distal annular portion may be larger than the proximal annular portion. The thrust bearing and soft member may be annular. The thrust bearing and soft member may be received about the proximal annular portion of the rigid member.

A trocar assembly for a surgical stapling instrument includes a housing, a trocar member, a drive member, and a bearing assembly. The housing includes a tubular body having a proximal portion and a distal portion, and a flange. The trocar member slidably supported within the housing and movable between a retracted position and an advanced position. The drive member is in operable engagement with the trocar member to cause longitudinal movement of the trocar member relative to the housing between the advanced position and the retracted position. The drive member also includes a flange. The bearing assembly is disposed within the housing between the flange of the housing and the flange of the drive member. The bearing assembly is configured to rotatably support the drive member and includes a thrust bearing, a rigid member, and a compressible member disposed between the thrust bearing and the rigid member. The rigid member is spaced from the flange of the drive member during a clamping stroke of the surgical stapling instrument and the rigid member engages the flange of the drive member during a stapling stroke of the surgical stapling instrument.

In certain aspects of the disclosure, the compressible member includes a first compressed condition having a first thickness during the clamping stroke of the surgical stapling instrument and a second compressed condition having a second thickness during the stapling stroke of the surgical stapling instrument. The second thickness may be less than the first thickness. The compressible member may include an uncompressed condition. The compressible member may transition from the uncompressed condition to the first compressed condition as the trocar member moves from the advanced position to the retraction position. The rigid member may include a proximal annular portion and a distal annular portion. The distal annular portion may be larger than the proximal annular portion. The thrust bearing and soft member may be annular. The thrust bearing and soft member may be received about the proximal annular portion of the rigid member.

A surgical stapling instrument having a clamping stroke and a stapling stroke includes an adapter assembly and a trocar assembly disposed within the adapter assembly. The trocar assembly includes a housing, a trocar member, a drive member, and a bearing assembly. The housing includes a tubular body having a proximal portion and a distal portion, and a flange. The trocar member is slidably supported within the housing and is movable between a retracted position and an advanced position. The drive member is in operable engagement with the trocar member to cause longitudinal movement of the trocar member relative to the housing between the advanced position and the retracted position. The drive member also includes a flange. The bearing assembly is disposed within the housing between the flange of the housing and the flange of the drive member. The bearing assembly is configured to rotatably support the drive member and includes a thrust bearing, a rigid member, and a compressible member disposed between the thrust bearing and the rigid member. The rigid member is spaced from the flange of the drive member during the clamping stroke and engages the flange of the drive member during the stapling stroke.

In some aspects of the disclosure, the trocar assembly is releasable from the adapter assembly. The surgical stapling instrument may further include a handle assembly. The adapter assembly may be releasably securable to the handle assembly. The surgical stapling instrument may further include an anvil assembly supported on the trocar member.

A trocar assembly for a surgical stapling instrument includes a housing, a trocar member slidably supported within the housing and movable between a retracted position and an advanced position, and a drive member in operable engagement with the trocar member to cause longitudinal movement of the trocar member relative to the housing between the advanced position and the retracted position the trocar assembly. The housing includes a tubular body and a flange, the housing having a proximal portion and a distal portion. The drive member includes a proximal portion. The trocar assembly further includes a bearing assembly disposed within the housing and operably secured to the proximal portion of the drive member. The bearing assembly is configured to rotatably support the drive member and includes a base member, a thrust bearing, and at least one conical washer. The at least one conical washer is deformable from a first configuration having a first height during a clamping stroke of the surgical stapling instrument to a second configuration having a second height during a stapling stroke of the surgical stapling instrument. The second height is less than the first height.

In some aspects of the disclosure, the base member includes an extension portion and the at least one conical washer includes an inner portion and an outer portion. The inner portion of a first conical washer of the at least one conical washer may be spaced from the extension portion of the base member in the first configuration of the at least one conical washer. The inner portion of the first conical washer of the at least one conical washer may engage the extension portion of the base member in the second configuration of the plurality of conical washers. The at least one conical washer may include five (5) conical washers. The extension portion of the base member may be flared. The at least one conical washer may be a Belleville washer. The base member may include a body portion, a drive portion, and an extension portion. The drive portion may be configured for operable engagement with a drive shaft assembly.

In certain aspects of the disclosure, the thrust bearing includes a first height and the extension portion of the base member includes a second height. The first height may be the same as the second height. Alternatively, the first height is less than the second height.

A surgical stapling instrument having a clamping stroke and a stapling stroke includes an adapter assembly; and a trocar assembly disposed within the adapter assembly. The trocar assembly includes a housing, a trocar member slidably supported within the housing and movable between a retracted position and an advanced position, and a drive member in operable engagement with the trocar member to cause longitudinal movement of the trocar member relative to the housing between the advanced position and the retracted position the trocar assembly. The housing includes a tubular body and a flange, the housing having a proximal portion and a distal portion. The drive member includes a proximal portion. The trocar assembly further includes a bearing assembly disposed within the housing and operably secured to the proximal portion of the drive member. The bearing assembly is configured to rotatably support the drive member and includes a base member, a thrust bearing, and at least one conical washer. The at least one conical washer is deformable from a first configuration having a first height during a clamping stroke of the surgical stapling instrument to a second configuration having a second height during a stapling stroke of the surgical stapling instrument. The second height is less than the first height.

BRIEF DESCRIPTION OF THE DRAWINGS

The accompanying drawings, which are incorporated in and constitute a part of this specification, illustrate aspects of the disclosure and, together with a general description of the disclosure given above, and the detailed description of the aspects given below, serve to explain the principles of the disclosure, wherein.

DETAILED DESCRIPTION

Figure 1:
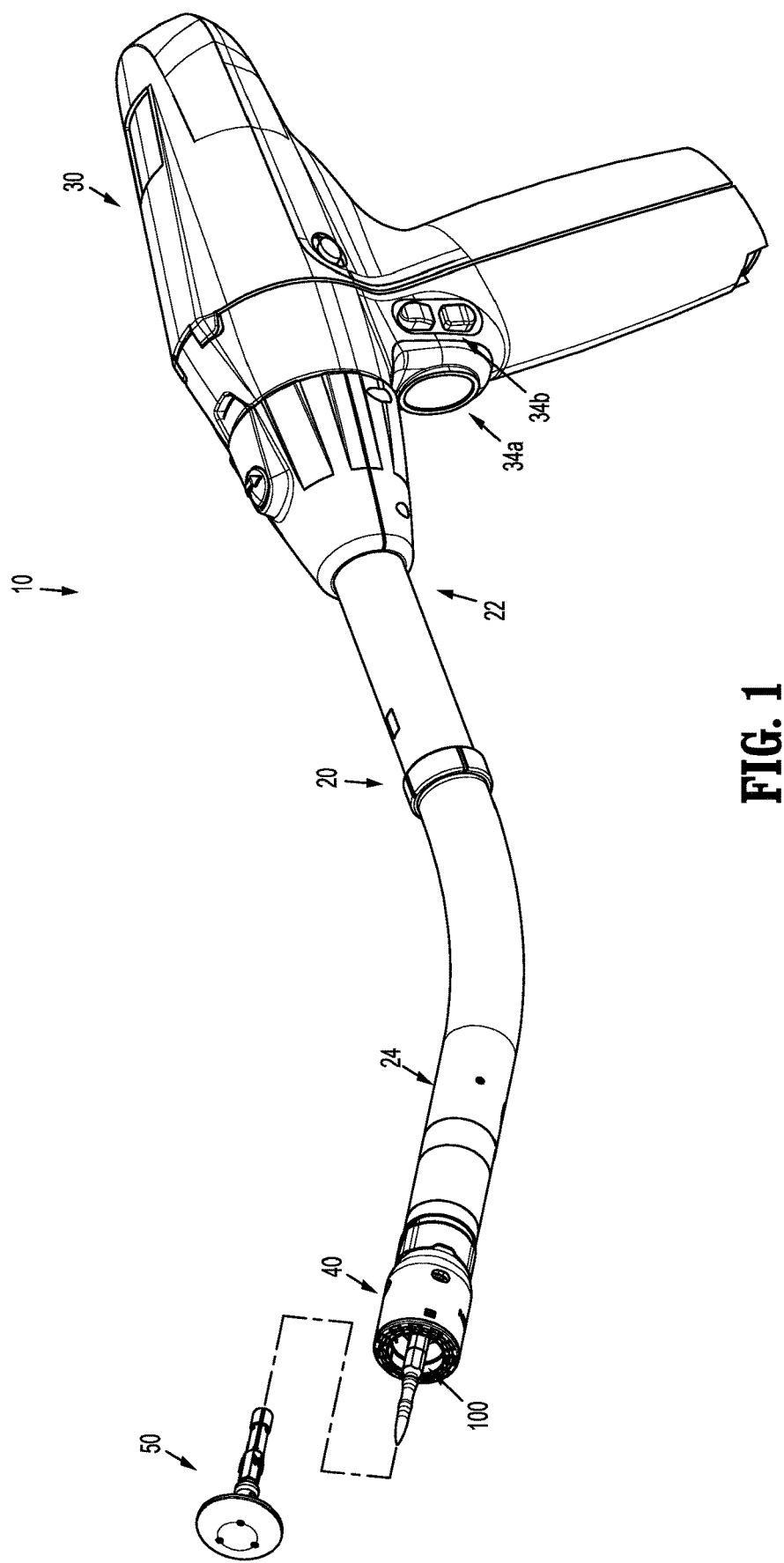
FIG. 1 is a side perspective view of a surgical stapling instrument including a trocar assembly according to aspects of the disclosure.

The disclosed surgical stapling instrument will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, and similar terms are used to assist in understanding the description and are not intended to limit the disclosure.

In this description, the term "proximal" is used generally to refer to that portion of the instrument that is closer to a clinician, while the term "distal" is used generally to refer to that portion of the instrument that is farther from the clinician. In addition, the term "clinician" is used generally to refer to medical personnel including doctors, nurses, and support personnel.

Terms including "generally," "about," "substantially," and the like, as utilized herein, are meant to encompass variations, e.g., manufacturing tolerances, material tolerances, use and environmental tolerances, measurement variations, and/or other variations, up to and including plus or minus 10 percent (±10%).

The disclosed surgical stapling instrument includes a trocar assembly and a mechanism for distributing the increased load that occurs during stapling and/or cutting of tissue.

FIG. 1 illustrates a surgical stapling instrument 10 including an adapter assembly 20 having a trocar assembly according to aspects of the disclosure. The surgical stapling instrument 10 further includes a powered handle assembly 30, a loading unit 40, and an anvil assembly 50. Although shown and described with reference to surgical stapling instrument 10, the aspects of the disclosure may be modified for use with surgical stapling instruments having alternative configurations. For example, the adapter assembly 20 may be configured as a component in a robotic system, or with manual actuation. The handle assembly 30 include a stationary grip 32 that supports actuation buttons 34a, 34b for controlling operation of various functions of the stapling device 10 including clamping, stapling, and cutting of tissue.

The adapter assembly 20 of the surgical stapling instrument 10 will only be described to the extent necessary to fully disclose the aspects of the disclosure. For a detailed description of exemplary adapter assemblies, please refer to commonly owned U.S. Pat. Nos. 10,226,254 and 10,111,684 ("the '684 patent").

The adapter assembly 20 includes a proximal portion 22 configured for operable connection to the handle assembly 30 and a distal portion 24 configured for operable connection to the loading unit 40. Although shown as forming an integral unit, it is envisioned that the proximal and distal portions 22, 24 of the adapter assembly 20 may be formed as separate units that are releasably securable to one another.

A trocar assembly 100 extends distally from the distal portion 24 of the adapter assembly 20 of the surgical stapling instrument 10 and is releasably secured within the distal portion 24 of the adapter assembly 20 by a locking mechanism (not shown). The trocar assembly 100 is configured to position the anvil assembly 50 relative to the loading unit 40. It is envisioned that the aspects of the disclosure may be incorporated into a trocar assembly 100 that is integrally formed with the adapter assembly. For a detailed description of an exemplary locking mechanism for securing the trocar assembly 100 within the distal portion 24 of the adapter assembly 20, please refer to the '684 patent.

Figure 2:
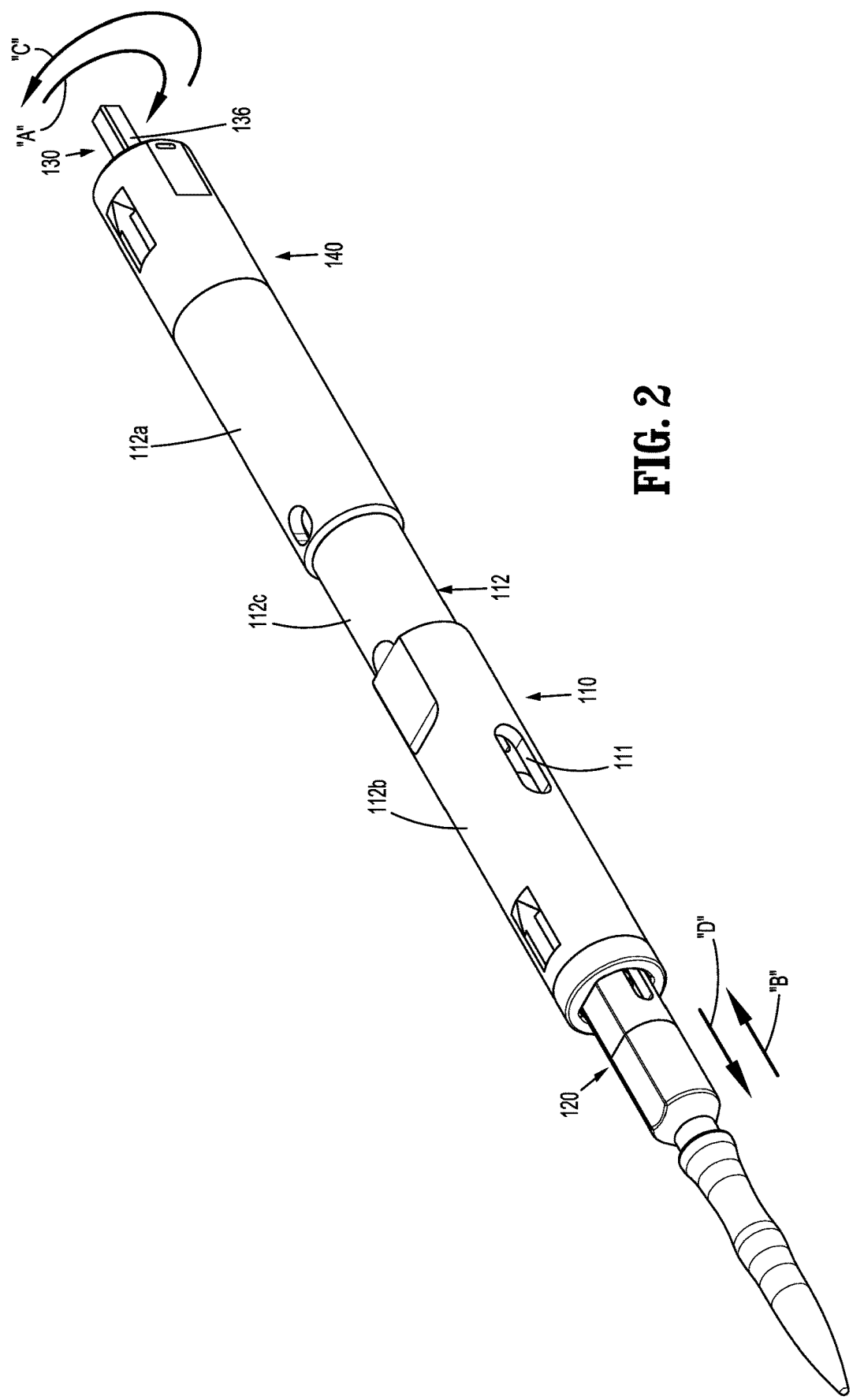
FIG. 2 is a perspective view of the trocar assembly of the surgical stapling instrument shown in FIG. 1.
Figure 3:
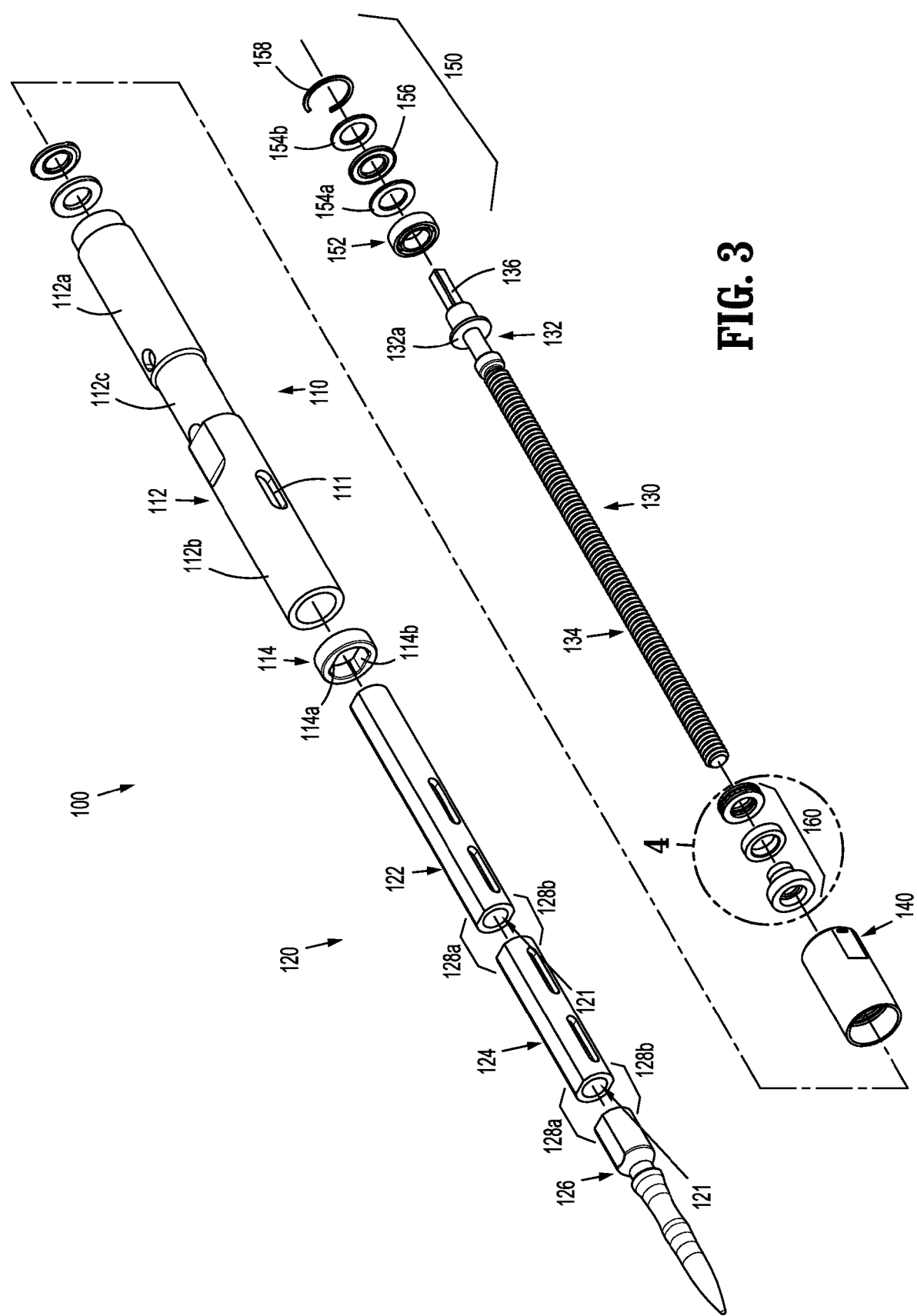
FIG. 3 is a perspective view of the trocar assembly shown in FIG. 2, with parts separated.

FIGS. 2 and 3 illustrate the trocar assembly 100 of the adapter assembly 20 (FIG. 1) of the surgical stapling instrument 10 (FIG. 1) which includes a trocar housing 110, a trocar member 120, and a drive member 130. The trocar member 120 is extendable from within the trocar housing 110. The drive member 130 is rotatably supported within an extension 140 of trocar housing 110 by proximal and distal bearing assemblies 150, 160 (FIG. 3) and is in operable engagement with the trocar member 120. Rotation of the drive member 130 of the trocar assembly 100 in a first rotational direction, i.e., clockwise, as indicated by arrow "A" in FIG. 2, causes longitudinal movement of the trocar member 120 in a first longitudinal direction, i.e., retraction, as indicated by arrow "B". Conversely, rotation of the drive member 130 of the trocar assembly 100 in a second rotational direction, i.e., counter-clockwise, as indicated by arrow "C" in FIG. 2, causes longitudinal movement of the trocar member 120 in a second longitudinal direction, i.e., advancement, as indicated by arrow "D".

The trocar housing 110 of the trocar assembly 100 includes a substantially tubular body 112 having proximal, distal, and central portions 112a, 112b, 112c. In certain aspects of the disclosure, and as shown, the tubular body 112 of the trocar housing 110 defines a pair of slots 111 to facilitate releasable attachment of the trocar assembly 100 within the distal portion 24 (FIG. 1) of the adapter assembly 20 of the surgical stapling instrument 10. Alternatively, the tubular body 112 of the housing 110 may include tabs, slots and tabs, threading, or other suitable feature for releasable attachment of the trocar assembly 100 to the adapter assembly 20. Alternatively, the trocar housing 110 may be integrally formed with the adapter assembly 20, and thus not removable from the adapter assembly 20.

The trocar assembly 100 of the surgical stapling instrument 10 includes a distal end cap member 114 (FIG. 3) disposed on the distal portion 112b of the tubular body 112. The distal end cap 114 supports the trocar member 120 of the trocar assembly 100 as the trocar member 120 moves longitudinally relative to the trocar housing 110. The distal end cap member 114 includes first and second flattened inner surfaces 114a (FIG. 7), 114b.

The trocar member 120 of the trocar assembly 100 includes an elongate body portion 122, an extension portion 124 extending from the elongate body portion 122, and a trocar spike 126 supported on an end of the extension portion 124. Although shown as separate components, it is envisioned that the elongate body portion 122, the extension portion 124, and/or the trocar spike 126 may be integrally formed with each other and may be formed of the same or different materials.

The trocar spike 126 of the trocar member 120 is configured to penetrate tissue and permit releasable engagement of the trocar spike 126 with an anvil assembly, e.g., the anvil assembly 50 (FIG. 1). Each of the elongate body portion 122, the extension portion 124, and the trocar spike 126 of the trocar member 120 includes first and second flattened outer surfaces 128a, 128b. The first and second flattened outer surfaces 128a, 128b of the trocar member 120 align with first and second flattened inner surfaces 114a, 114b of the distal end cap member 114. Engagement of the first and second outer surfaces 128a, 128b of the trocar member 120 with the respective first and second flattened inner surfaces 114a, 114b of the distal end cap 114 prevents the trocar member 120 from rotating about its longitudinal axis as the trocar member 120 moves longitudinally relative to the trocar housing 110. The trocar member 120 defines a longitudinal channel 121 (FIG. 6) including at least a portion that is threaded, i.e., threaded portion 121a, (FIG. 6) for operably receiving, and engaging, the drive member 130.

The drive member 130 of the trocar assembly 100 includes a flange portion 132 (FIG. 3) having a flange 132a, a threaded portion 134 extending distally from the flange portion 132, and a drive portion 136 extending proximally from the flange portion 132. The threaded portion 134 of the drive member 130 is received in the longitudinal channel 121 of the trocar member 120 and engages the threaded portion 121a of the trocar member 120.

The flange 132a of the flange portion 132 of the drive member 130 is supported between the proximal and distal bearing assemblies 150 (FIG. 3), 160. As detailed above, during a stapling procedure, the drive member 130 is rotated in a first direction to cause the retraction of the anvil assembly 50 relative to the loading unit 40 and clamping of tissue (not shown) between the loading unit 40 (FIG. 1) and the anvil assembly 50. Thus, the drive member 130 experiences dynamic loading during clamping of tissue. Subsequently, the drive member 130 remains stationary during the stapling and/or cutting of tissue. Thus, the drive member 130 experiences static loading during stapling and/or cutting of clamped tissue. The stapling and cutting of tissue may occur simultaneously or sequentially. The forces experienced by the drive member 130 of the trocar assembly 120 during the stapling and/or cutting of tissue are substantially greater than the force experienced by the drive member 130 during clamping of tissue.

During a stapling procedure, the thrust force or load experienced by the drive member 130 of the trocar assembly 120 is transferred to the adapter assembly 20 (FIG. 1) through the bearing assembly 150. Accordingly, certain aspects of the disclosure are directed to the bearing assembly 150. The proximal bearing assembly 150 may include any conventional bearing assembly suitable for operation in cooperation with the bearing assembly 150 to facilitate rotation of the drive member 130 during a stapling procedure. As shown, the proximal bearing assembly 150 includes a bearing member 152, first and second spacers 154a, 154b, a friction plate 156 disposed between the first and second spacers 154a, 154b, and a locking clip or ring 158. For a detail description of an exemplary proximal bearing assembly 150, please refer to U.S. Pat. No. 10,226,254.

Figure 4:
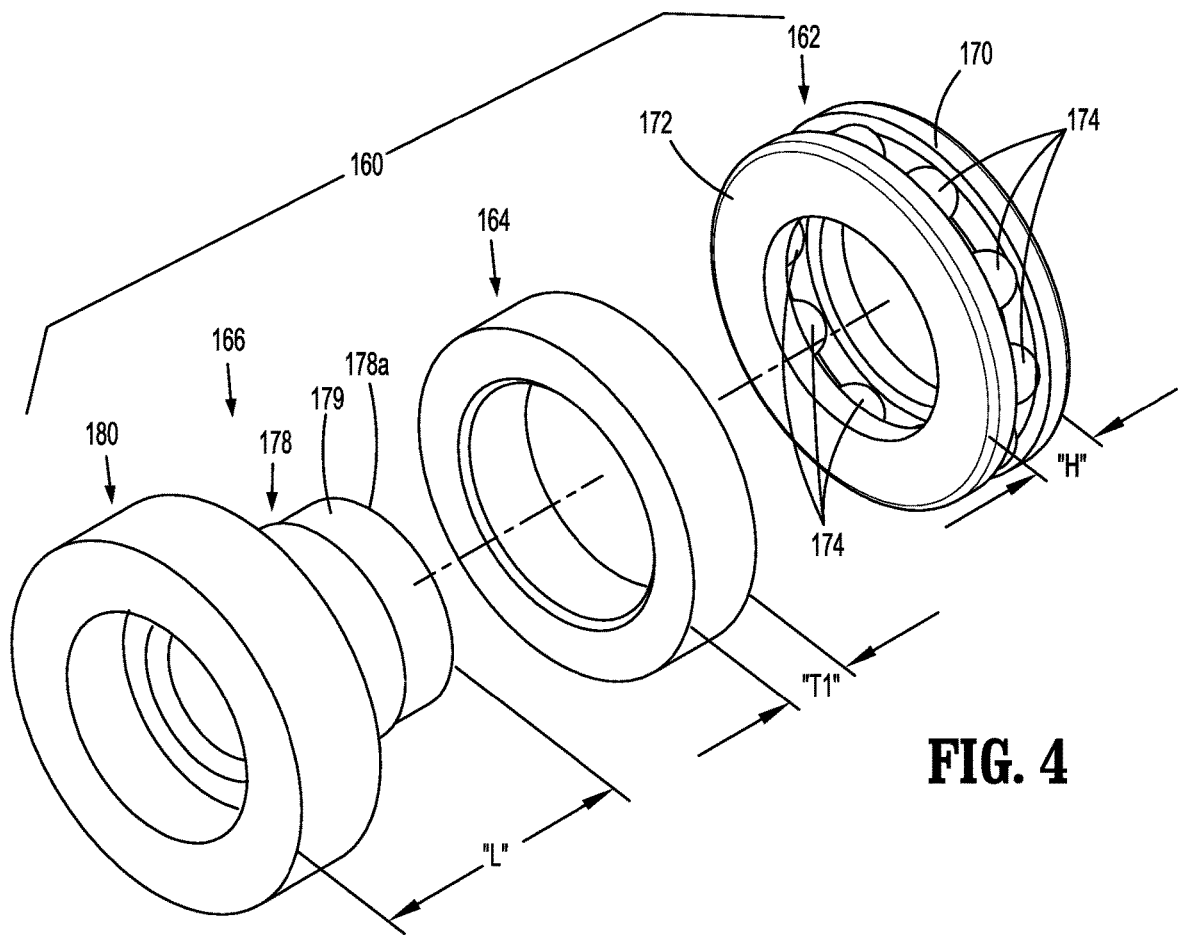
FIG. 4 is an enlarged view of the indicated area of detail shown in FIG. 3.

FIG. 4 illustrates the bearing assembly 150. The bearing assembly 150 includes a thrust bearing 154, a soft bearing support 164, and a rigid bearing support 166. The thrust bearing 154 may be any commercially available thrust bearing, and as shown, includes a proximal plate 170, a distal plate 172, and a plurality of ball bearings 174 supported between the proximal and distal plates 170, 172. The thrust bearing 154 is configured to provide smooth, low friction rotation of the drive member 130 during axial loading, i.e., as the drive member 130 is rotated during the clamping of tissue. The thrust bearing 154 includes a height "H". Although the thrust bearing 154 is shown as a thrust ball bearing, it is envisioned that the thrust bearing 154 may include other types of bearings capable of handling axial loads, e.g., roller thrust bearing.

The thrust bearing 154 of the bearing assembly 150 is configured to accommodate the load experienced by the drive member 130 during clamping of tissue, e.g., about 250 lbs. The thrust bearing 154 becomes less effective during axial loading in excess of that experienced by the drive member 130 during clamping of tissue. A thrust bearing having a size capable of handling the static loads experienced by the drive member 130 during stapling and/or cutting of tissue, e.g., about 600 lbs. for stapling and 300 lbs. for cutting, would be excessively large, and therefore, not practical. Overloading of the thrust bearing 154 may be detrimental to the operation of the thrust bearing 154 and may result in malfunction of the surgical stapling instrument 10 (FIG. 1).

Figure 10:
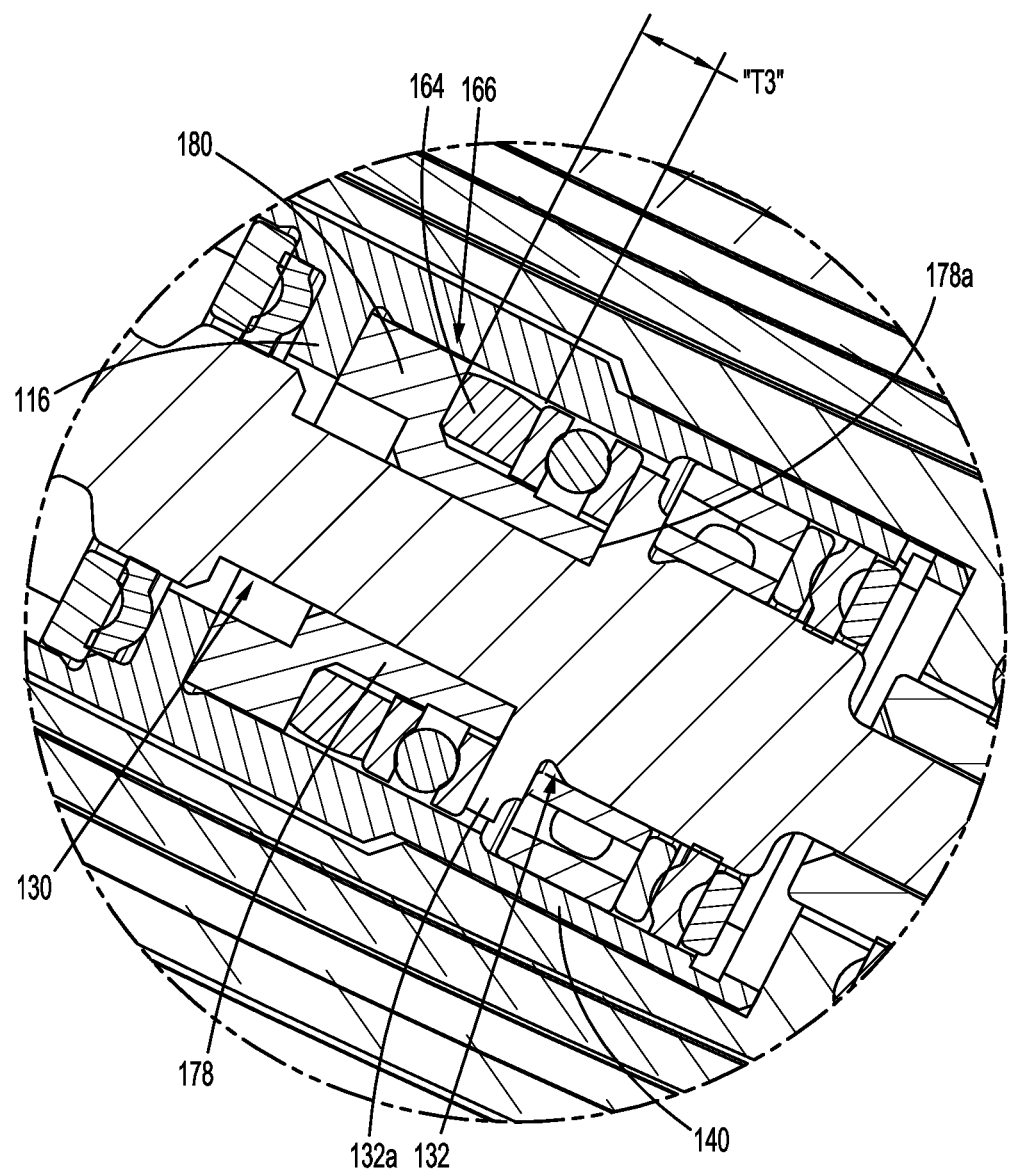
FIG. 10 is an enlarged view of the indicated area of detail shown in FIG. 9.

The soft bearing support member 164 of the bearing assembly 150 includes a compressible annular member formed of one or more compressible materials. The soft bearing support 164 is configured to compress during axial loading. The soft bearing support member 164 includes an uncompressed condition having a first thickness "T1", a first compressed condition (FIG. 7) having a second thickness "T2", and a second compressed condition (FIG. 10) having a third thickness "T3". Although shown having a substantially annular body with a substantially rectangular cross-section, it is envisioned that the soft bearing support member 164 may include other configurations, e.g., substantial toroidal, and substantially circular. It is envisioned that the soft bearing support member 164 may be replaced by a compression spring, e.g., coil or wave springs, or other suitable spring with a comparable compression profile.

The rigid bearing support member 166 includes a proximal annular portion 178 and a distal annular portion 180 and may be formed of hard plastic, metal, or other suitable rigid material. The rigid bearing support member 166 may be formed of unity construction, or multiple components secured relative to one another. The proximal annular portion 178 of the rigid bearing support member 166 includes a diameter that is smaller than a diameter of the distal annular portion 180 and is configured to support the soft bearing support member 164 and the thrust bearing 154. The proximal annular portion 178 of the rigid bearing support member 166 includes a length "L" equal to the combined length of the second, compressed thickness "T3" (FIG. 10) of the soft bearing support member 164 and the height "H" of the thrust bearing 154. The proximal annular portion 178 includes a distal end 178a and may include an annular notch or cutout 179.

Figure 5:
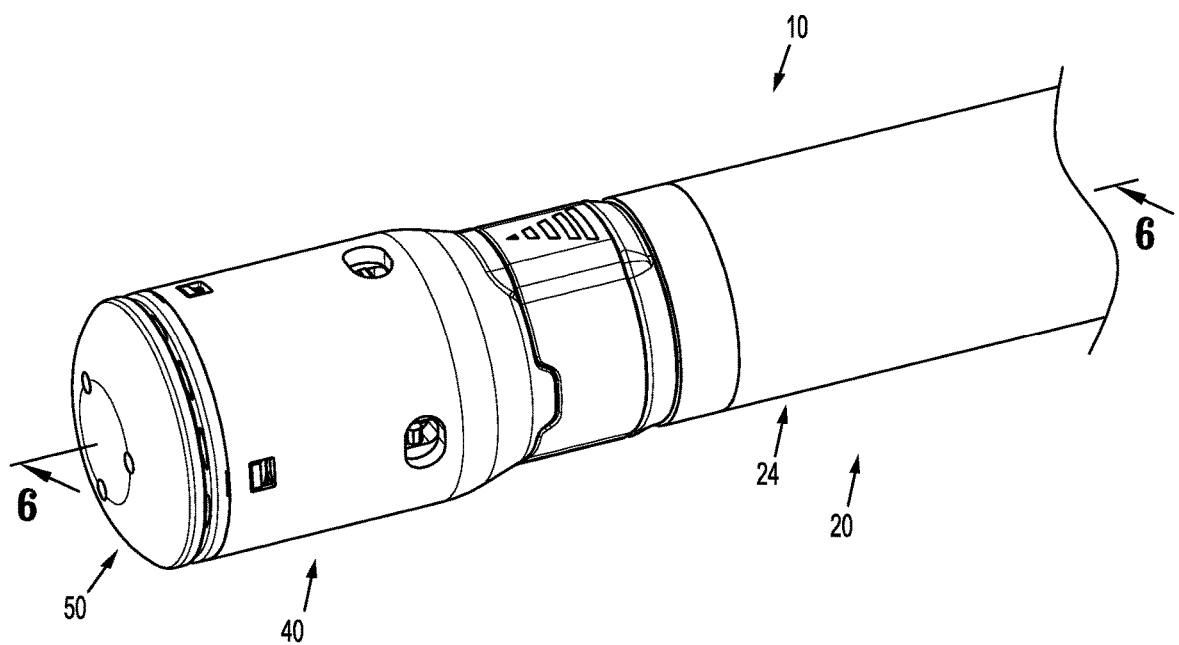
FIG. 5 is a side perspective view of a distal end of the surgical stapling instrument shown in FIG. 1, with the anvil assembly in a clamped position.
Figure 6:
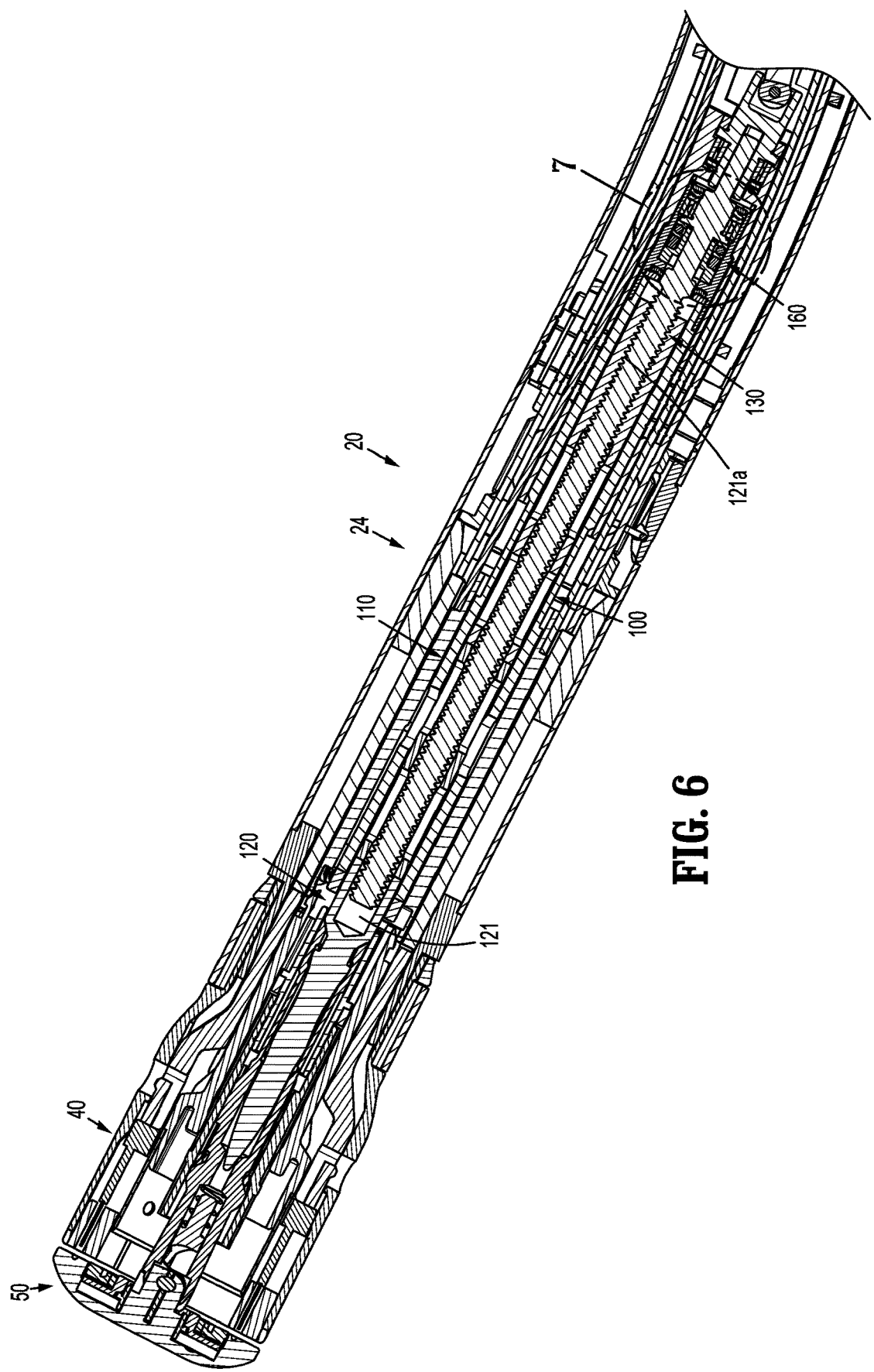
FIG. 6 is a cross-sectional side view taken along section line 6-6 shown in FIG. 5.

FIGS. 5 and 6 illustrate the operational end of the surgical stapling instrument 10 (FIG. 1), including the distal portion 24 of the adapter assembly 20, the loading unit 40 secured to the adapter assembly 20, and the anvil assembly 50 secured to the adapter assembly 20. The trocar member 120 (FIG. 6) of the trocar assembly 100 is in its retracted position and the surgical stapling instrument 10 (FIG. 1) is in the clamped condition.

Figure 7:
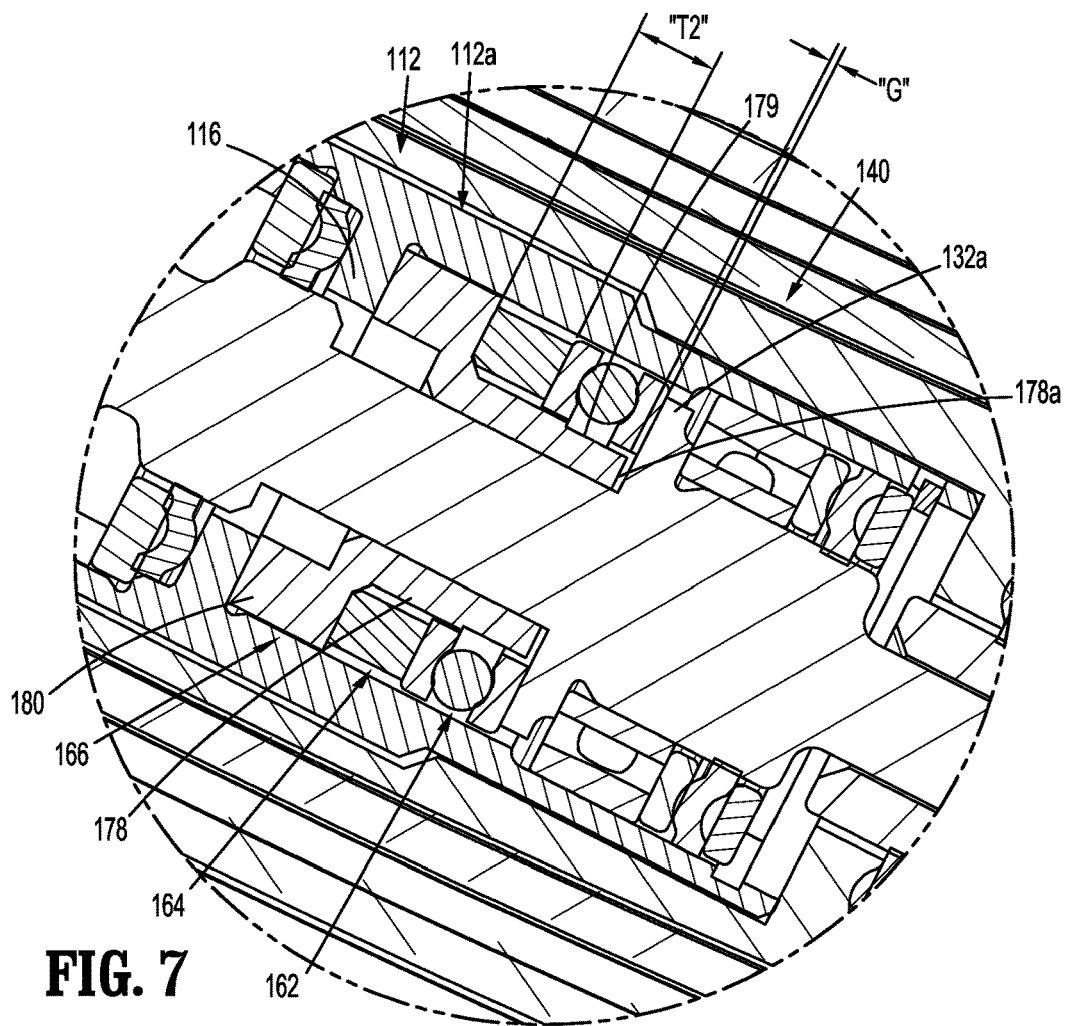
FIG. 7 is an enlarged view of the indicated area of detail shown in FIG. 6.
Figure 8:
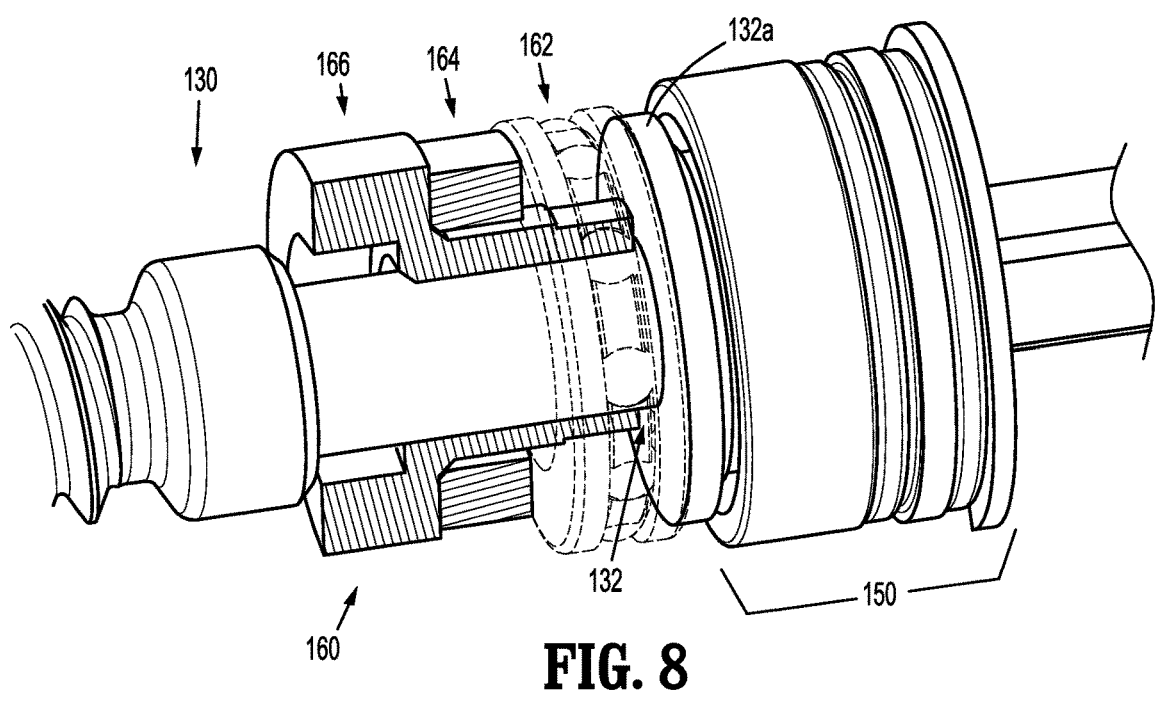
FIG. 8 is a side perspective view of a proximal and distal bearing assembly and drive member of the trocar assembly shown in FIG. 2, with a thrust bearing of the distal bearing assembly shown in phantom.
Figure 9:
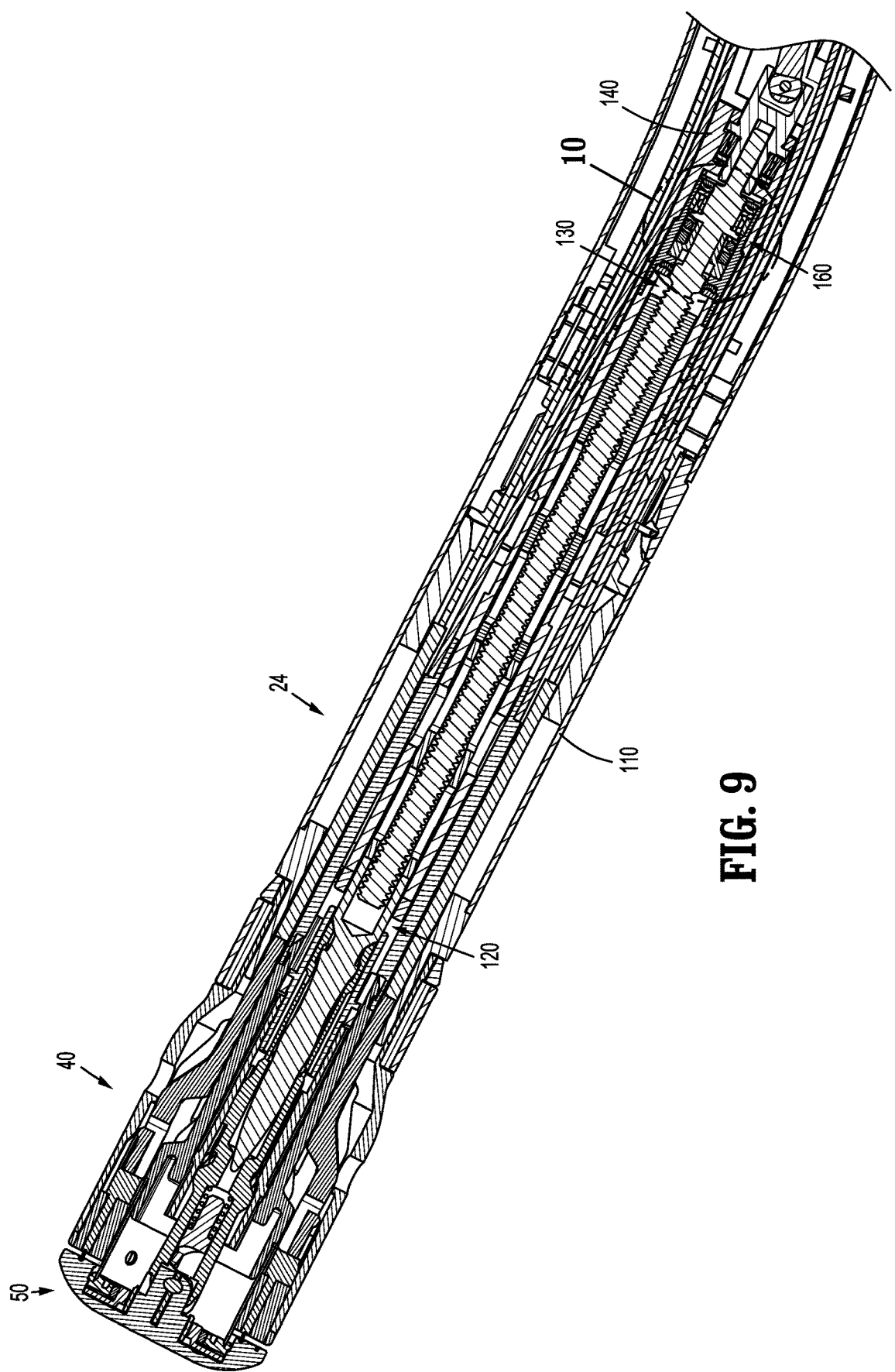
FIG. 9 is the cross-sectional side view shown in FIG. 6, during a stapling stroke of the surgical stapling instrument.

FIGS. 7 and 8 illustrate the proximal and distal bearing assemblies 150, 160 of the trocar assembly 100 supporting the drive member 130 of the trocar assembly 100 within the trocar housing 110 of the trocar assembly 100. The trocar member 120 is in the retracted position and the surgical stapling instrument 10 (FIG. 1) is in the clamped condition. The bearing assembly 150 is disposed within the proximal portion 112a (FIG. 7) of the tubular body 112 of the trocar housing 110 and the extension 140 of the trocar housing 110 and is positioned between a flange 116 of the trocar housing 110 and the flange 132a of the drive member 130. More particularly, the thrust bearing 154 is disposed distal of and in engagement with the flange 132a of the drive member 130, the soft bearing support member 164 is disposed distal of and in engagement with the thrust bearing 154, and the proximal annular portion 178 of the rigid bearing support member 166 is received through each of the soft bearing support member 164 and the thrust bearing 154 such that the distal annular portion 180 of the rigid bearing support member 166 is disposed distal of and in engagement with the soft bearing support member 164. The notch 179 in the proximal annular portion 178 of the rigid bearing support member 166 accommodates at least a portion of the thrust bearing 154.

Prior to the trocar member 120 moving to the retracted position, the soft bearing support member 164 is in the uncompressed condition (FIG. 4) and includes the first thickness "T1". When the soft bearing support member 164 is in the uncompressed condition, the proximal end 178a of the proximal annular portion 178 of the rigid bearing support member 166 is spaced a first distance (not shown) from the flange 132a of the flange portion 132 of the drive member 130. Because the rigid bearing support member 166 is spaced from the flange 132a of the drive member 130, any force experienced by the drive member 130 that is transferred to the bearing assembly 150 passes through the thrust bearing 154. As described above, the thrust bearing 154 is able to handle to lower forces experienced by the drive member 130 during clamping of tissue, and allows for a smooth, low friction rotation of the drive member 130 as the trocar member 120 is retracted.

During clamping of tissue, i.e., as the drive member 130 rotates and as the trocar member 120 retracts, the load on the drive member 130 increases as tissue is clamped between the anvil assembly 50 and the loading unit 40. The increasing load on the soft bearing support member 166 causes the soft bearing support member 166 to begin to compress. As the soft bearing support member 166 compresses under the increased load, the distance between the proximal end 178 of the proximal annular portion 178 of the rigid bearing support member 166 and the flange 132a of the flange portion 132 of the drive member 130 decreases. The compressibility of the soft bearing support member 166 is such that the width of the soft bearing support member 164 is enough that when the drive member 130 approaches the maximum clamping load during the clamping of tissue, the proximal end 178 of the proximal annular portion 178 remains spaced from, i.e., out of engagement with, the flange 132 of the drive member 130 forming a gap "G" (FIG. 7). In this manner, the thrust bearing 154 can continue providing smooth, low friction rotation of the drive member 130.

FIGS. 6 and 7 illustrate the adapter assembly 20 of the surgical stapling instrument 10 (FIG. 1) during a stapling stroke. During the stapling stroke, the trocar member 120 remains stationary and the drive member 130 is static. The increased load on the drive member 130 is transferred to the distal bearing assembly 150 which further compresses the soft bearing support member 164. Further compression of the soft bearing support member 164 causes the rigid bearing support member 166 to move proximally into engagement with the flange 132a of the drive member 130. Engagement of the rigid bearing support member 166 with the flange 132 allows for the rigid bearing support member 164 to support the continued axial loading of the drive member 130 through the remainder of the stapling and/or cutting strokes.

By diverting the increased load experienced by the drive member 130 during stapling and cutting of tissue, the rigid bearing support member 166 prevents the thrust bearing 154 from experiencing the increased loads, and thus not exceed its maximum operation load.

Subsequent to stapling and cutting tissue, the increased load experienced by the drive member 130 dissipates, and the soft bearing support member 164 can return to its first compressed condition. As the soft bearing support member 164 returns to the first compressed condition (FIG. 7), the rigid bearing support member 164 moves distally such that the proximal end 178a of the proximal annual portion 178 of the rigid bearing support member 164 moves out of engagement with the flange 132 of the drive member 130. In this manner, the rigid bearing support member 166 is no longer in position to support axial loading of the drive member 130. Unclamping of the surgical stapling instrument 10, i.e., rotating of the drive member 130 and advancing of the trocar member 120, allows the soft bearing support member 164 to return to its uncompressed condition (FIG. 4).

Figure 11:
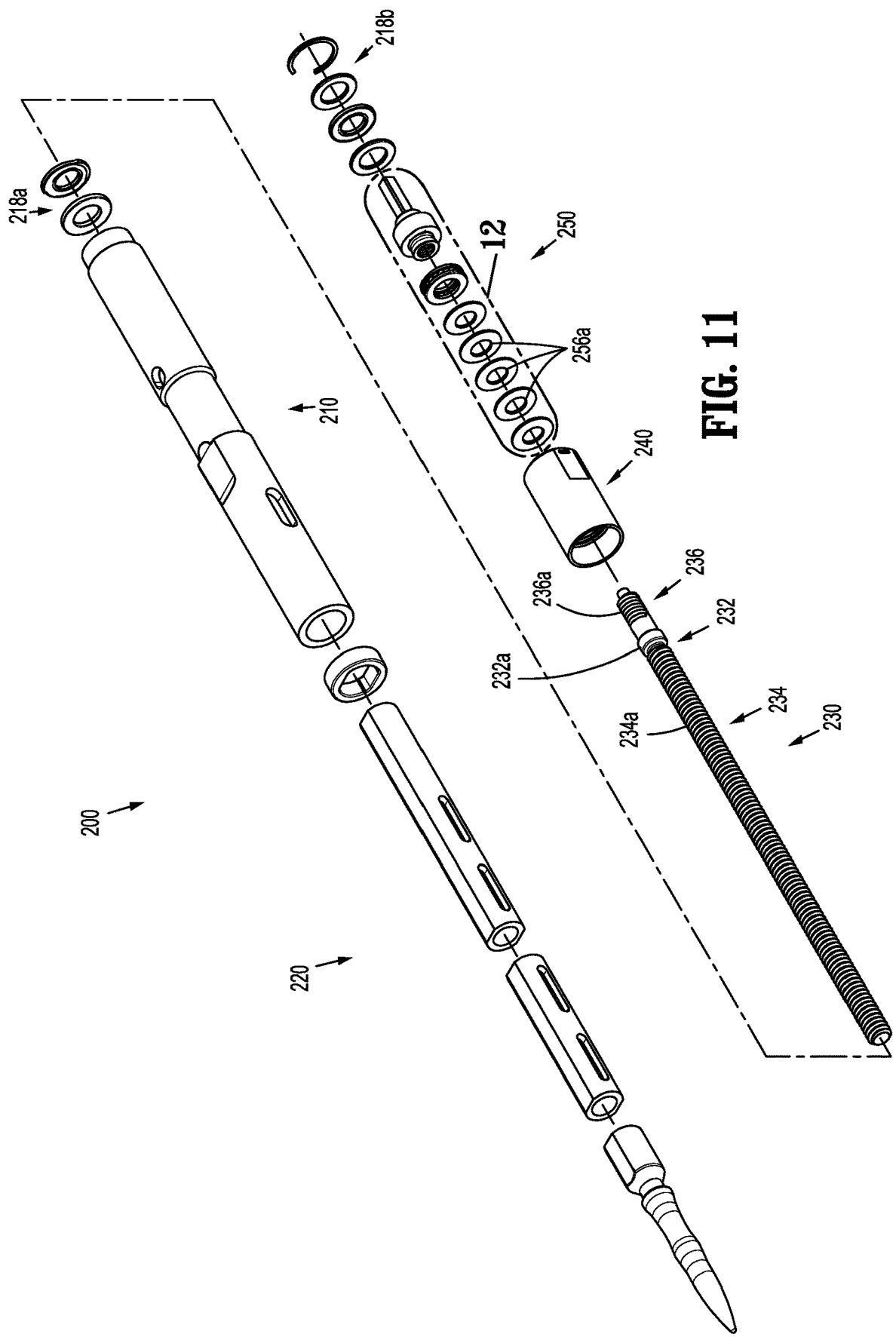
FIG. 11 is a perspective view of a trocar assembly according to another aspect of the disclosure, with parts separated.

FIG. 11 illustrates a trocar assembly according to another aspect of the disclosure, shown generally as trocar assembly 200. The trocar assembly 200 is substantially similar to the trocar assembly 100 described hereinabove and will only be described in detail as relates to the differences therebetween. The trocar assembly 200 includes a trocar housing 210, a trocar member 220, and a drive member 230. The trocar member 220 is selectively extendable from within the trocar housing 210 through rotation of the drive member 230. The drive member 230 is rotatably supported within an extension 240 of trocar housing 210 and is operably connected to a drive transfer or bearing assembly 250. The bearing assembly 250 of the trocar assembly 200 is retained within the extension 240 of the trocar housing 210 by a locking assembly 218b. The bearing assembly 250 supports the drive member 230 and provides a connection between the drive member 230 and a drive shaft assembly 30 (FIG. 13) of the adapter assembly 20 of the surgical stapling instrument 10 (FIG. 1). During a stapling procedure, the thrust force or load experienced by the drive member 230 of the trocar assembly 220 is transferred to the adapter assembly 20 (FIG. 1) through the bearing assembly 250.

The drive member 230 of the trocar assembly 200 includes a flange portion 232, a threaded portion 234 extending distally from the flange portion 232, and a connector portion 236 extending proximally from the flange portion 232. The flange portion 232 of the drive member 230 includes a flange 232a that is supported by a flange 216 (FIG. 14) of the trocar housing 210. A locking assembly 218a secures the drive member 230 relative to the trocar housing 210. The connector portion 236 of the drive member 230 includes a threaded section 236a. The threaded section 236a of the connector portion 236 is configured to secure the drive member 230 relative to the bearing assembly 250.

Figure 12:
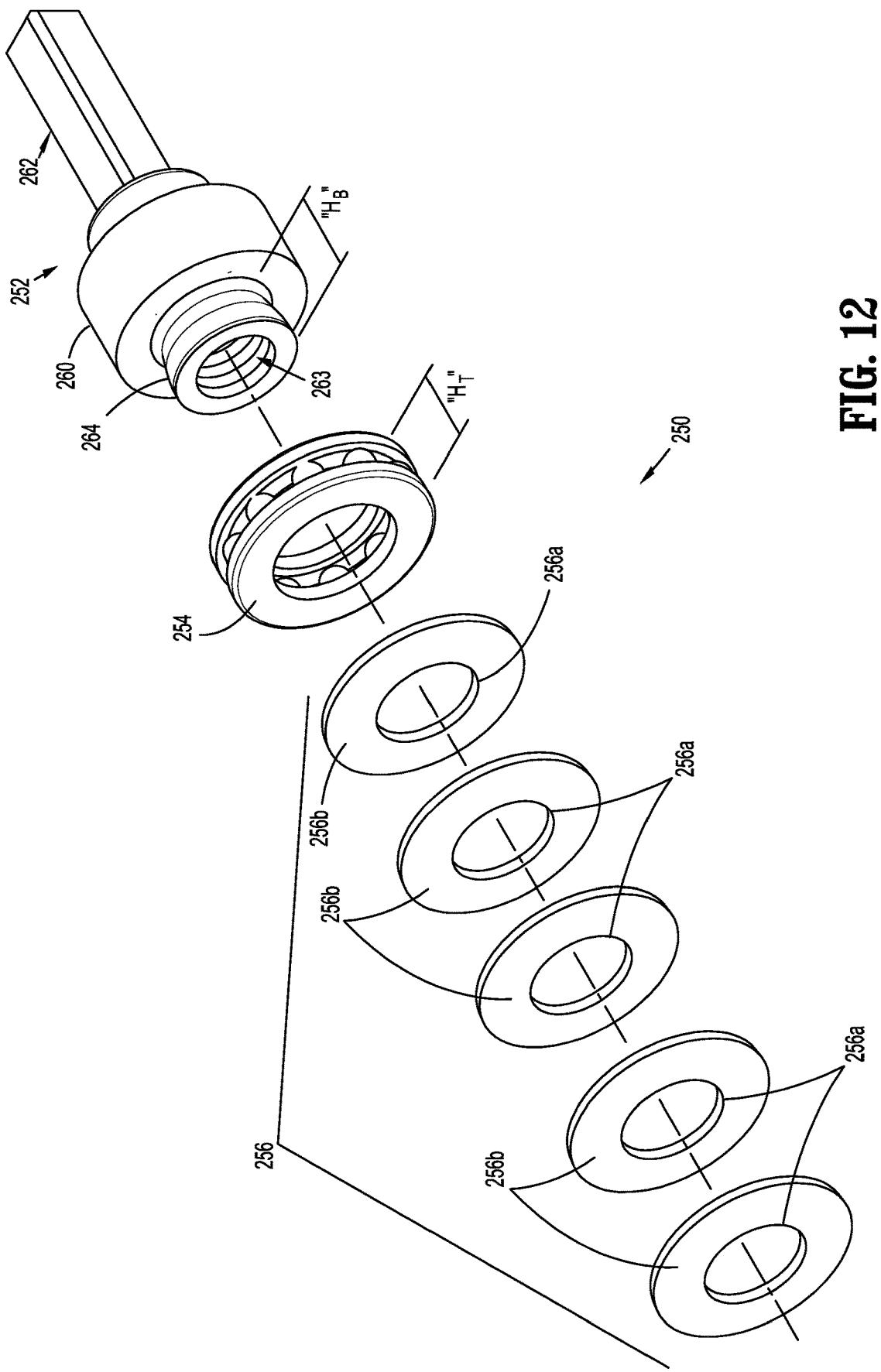
FIG. 12 is an enlarged view of the indicated area of detail shown in FIG. 11.

FIG. 12 illustrates the bearing assembly 250 of the trocar assembly 200 including a base or transfer member 252, a thrust bearing 254, and a plurality of Belleville or conical washers 256.

The base member 252 of the bearing assembly 250 includes a body portion 260, a drive portion 262 extending proximally from the body portion 260, and an extension portion 264 extending distally from the body portion 260. The body portion 260 and the extension portion 264 of the base member 252 define a threaded passage 263 for receiving the threaded section 236a of the connector portion 236 of the drive member 230 (FIG. 11). Although shown as including a threaded connection, it is envisioned that the drive member 230 may be secured to the base member 252 in any suitable manner. The drive portion 262 of the base member 252 is configured for operable connection with the drive shaft assembly 30 of the adapter assembly 20. The extension portion 264 of the base member 252 flares outwardly from the body portion 260 and is configured to support the thrust bearing 254. The extension portion 264 has a height "Hb".

The thrust bearing 254 of the bearing assembly 250 may be any commercially available thrust bearing that is configured to provide smooth, low friction rotation of the drive member 230 during axial loading of the trocar assembly 200, i.e., as the drive member 230 is rotated during clamping of tissue. The thrust bearing 254 includes a height "Ht". In certain aspects of the disclosure, the height "Ht" of the thrust bearing 254 is the same as the height "Hb" of the extension portion 264 of the base member 252. Alternatively, the height "Ht" of the thrust bearing 254 may be less than the height "Hb" of the extension portion 264 of the base member 252. As will become apparent from the below disclosure, the height "Hb" of the extension portion 264 and the height "Ht" of the thrust bearing 254 may be determined based on the amount of expected deformation of the plurality of Belleville washers 256 during high axial loads. Although the thrust bearing 254 is shown as a thrust ball bearing, it is envisioned that the thrust bearing 254 may include other types of bearings capable of handling axial loads, e.g., roller thrust bearing.

The plurality of Belleville washers 256 of the bearing assembly 250 may be any commercially available Belleville washers or other conical washers that are configured to deflect, or otherwise deform, under high axial loads. Although shown as having five (5) Belleville washers 256, it is envisioned that the bearing assembly 250 may have as few as one Belleville washer 256, and any additional number of Belleville washers 256. As will be described in further detail below, the Belleville washers 256 are configured such that the plurality of Belleville washers 256 includes a first configuration with a first effective height "h1" (FIG. 14). during low axial loads, and a second configuration with a second effective height "h2" (FIG. 17) during high axial loads. The first effective height "h1" is greater than the second effective height "h2". The conical shape of the Belleville washers 256 in the first configuration enables transfer of a load solely through outer portions 256b of the Belleville washers 256 during low axial loading, as an inner portion 256a of the Belleville washer 256 is longitudinally spaced from the outer portion 256b.

Figure 13:
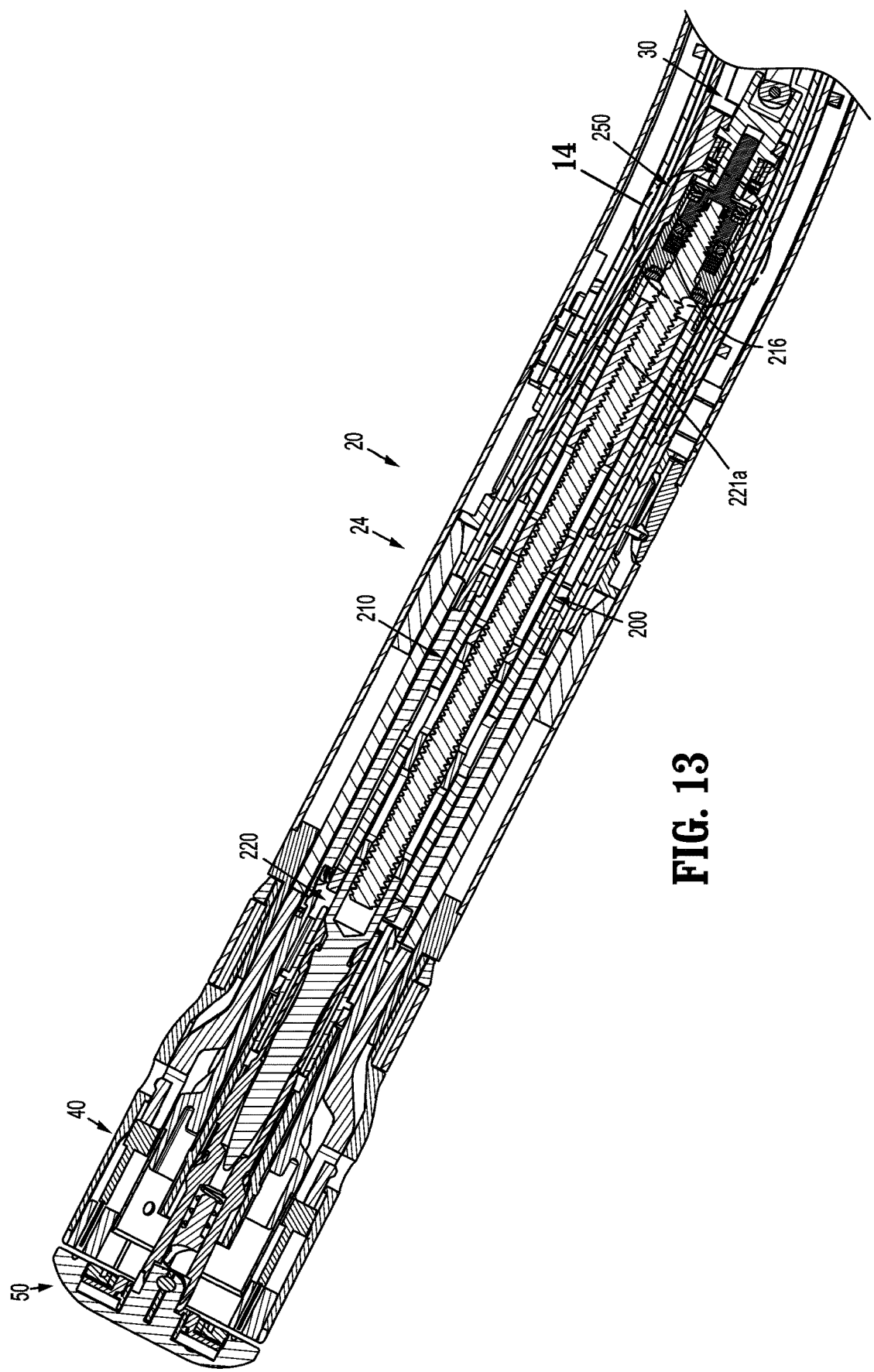
FIG. 13 is a cross-sectional side view of a distal end of a surgical stapling instrument including the trocar assembly shown in FIG. 12, with the anvil assembly in a clamped position.
Figure 14:
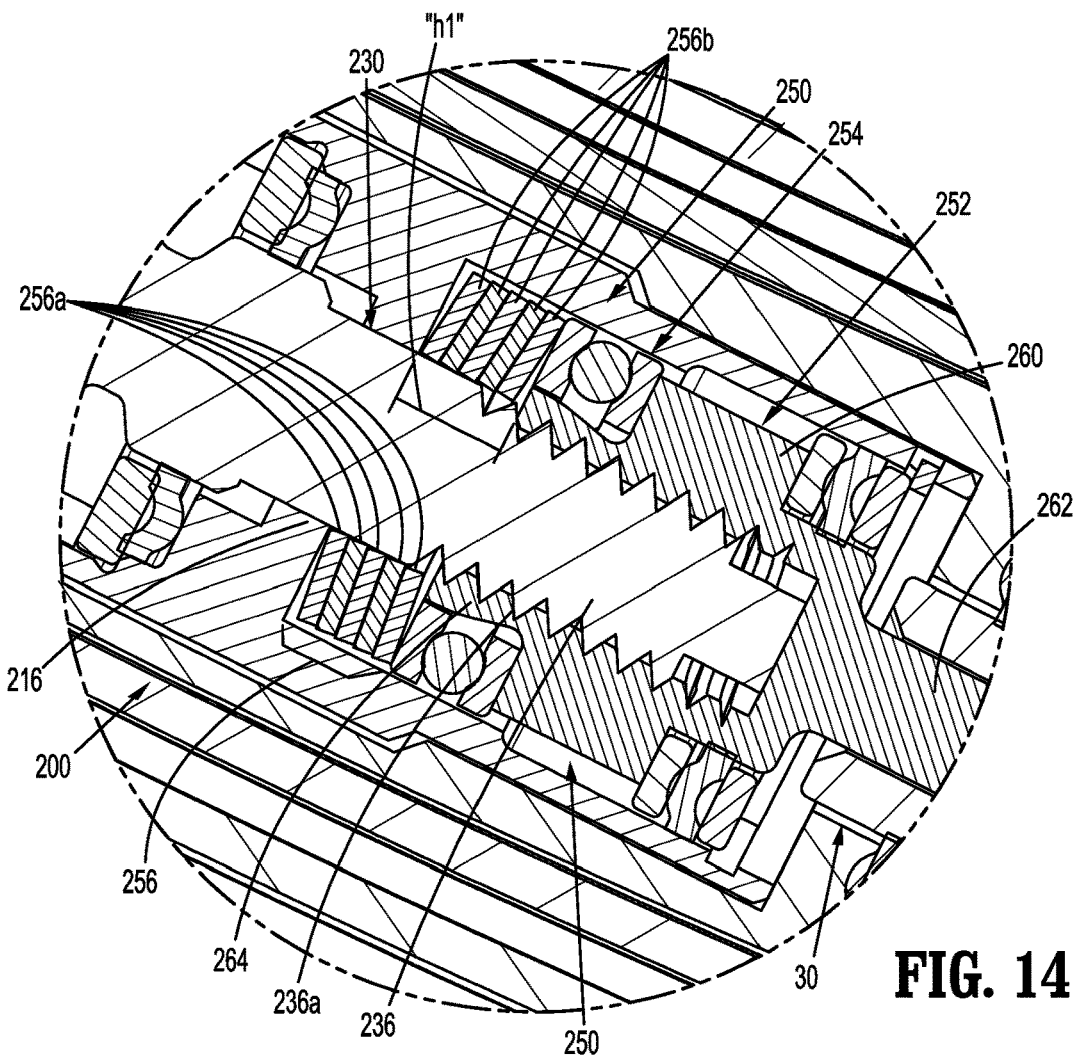
FIG. 14 is an enlarged view of the indicated area of detail shown in FIG. 13.
Figure 15:
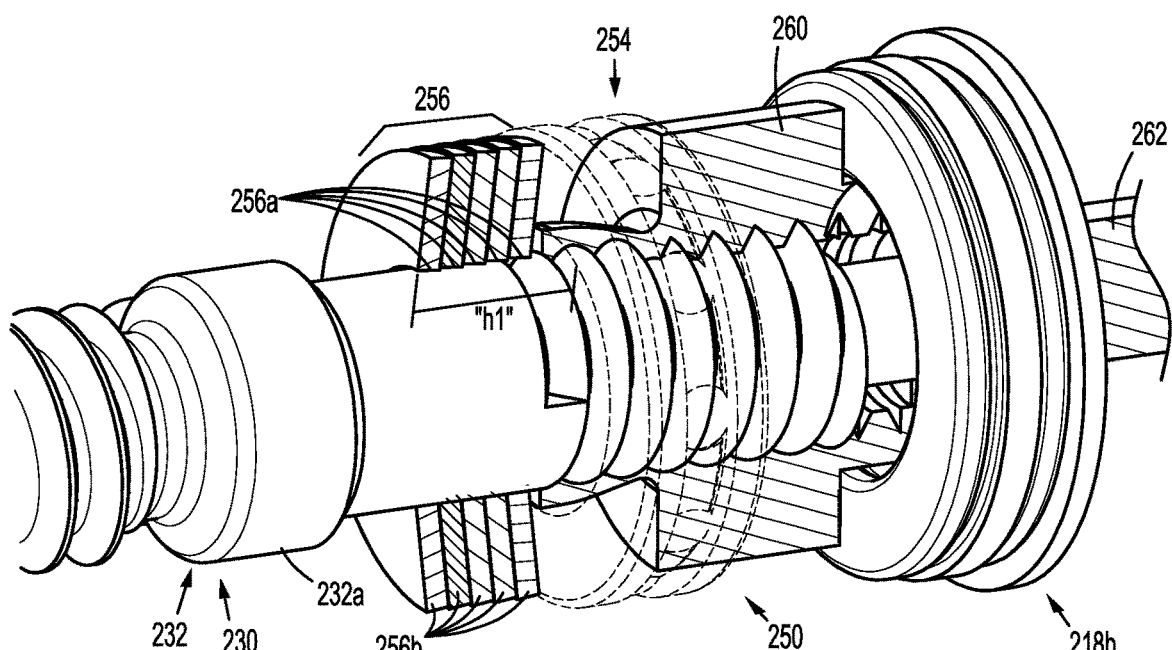
FIG. 15 is a perspective side view of a bearing assembly of the trocar assembly shown in FIG. 11.

FIGS. 13-15 illustrate the trocar assembly 200, and more particularly, the bearing assembly 250 of the trocar assembly 200 during clamping of tissue (not shown). During tissue clamping, the drive member 230 is rotated to cause the retraction of trocar member 220. Rotation of the drive member 230 is facilitated by the thrust bearing 254. More particularly, the axial load experienced by the drive member 230 during clamping is transferred from the base member 252 of the bearing assembly 250, through the thrust bearing 254 and the plurality Belleville washers 256, to the flange 216 of the adapter assembly 20. As noted above, during the clamping of tissue, the axial load experienced by the drive member 230 is between about 250 and about 300 lbs. At this lower axial load, the plurality of Belleville washers 256 has the first configuration with the first effective height "h1". In this manner, the outer portion 256b of the Belleville washer 256 engages the thrust bearing 254 and the inner portion 256a of the Belleville washer 256 is space from the extension portion 264 of the base member 252.

Figure 16:
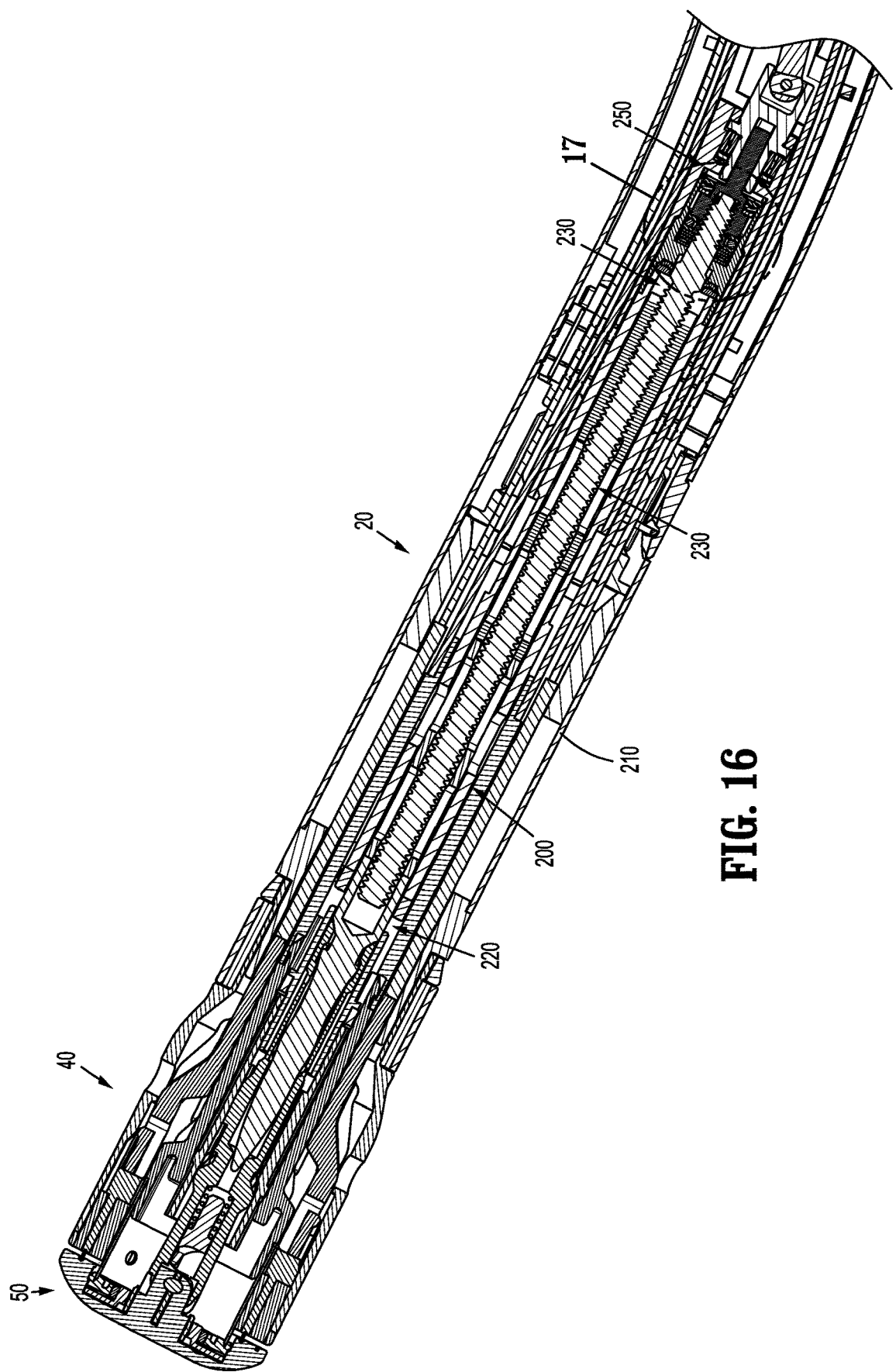
FIG. 16 is the cross-sectional side view shown in FIG. 13, during a stapling stroke of the surgical stapling instrument.
Figure 17:
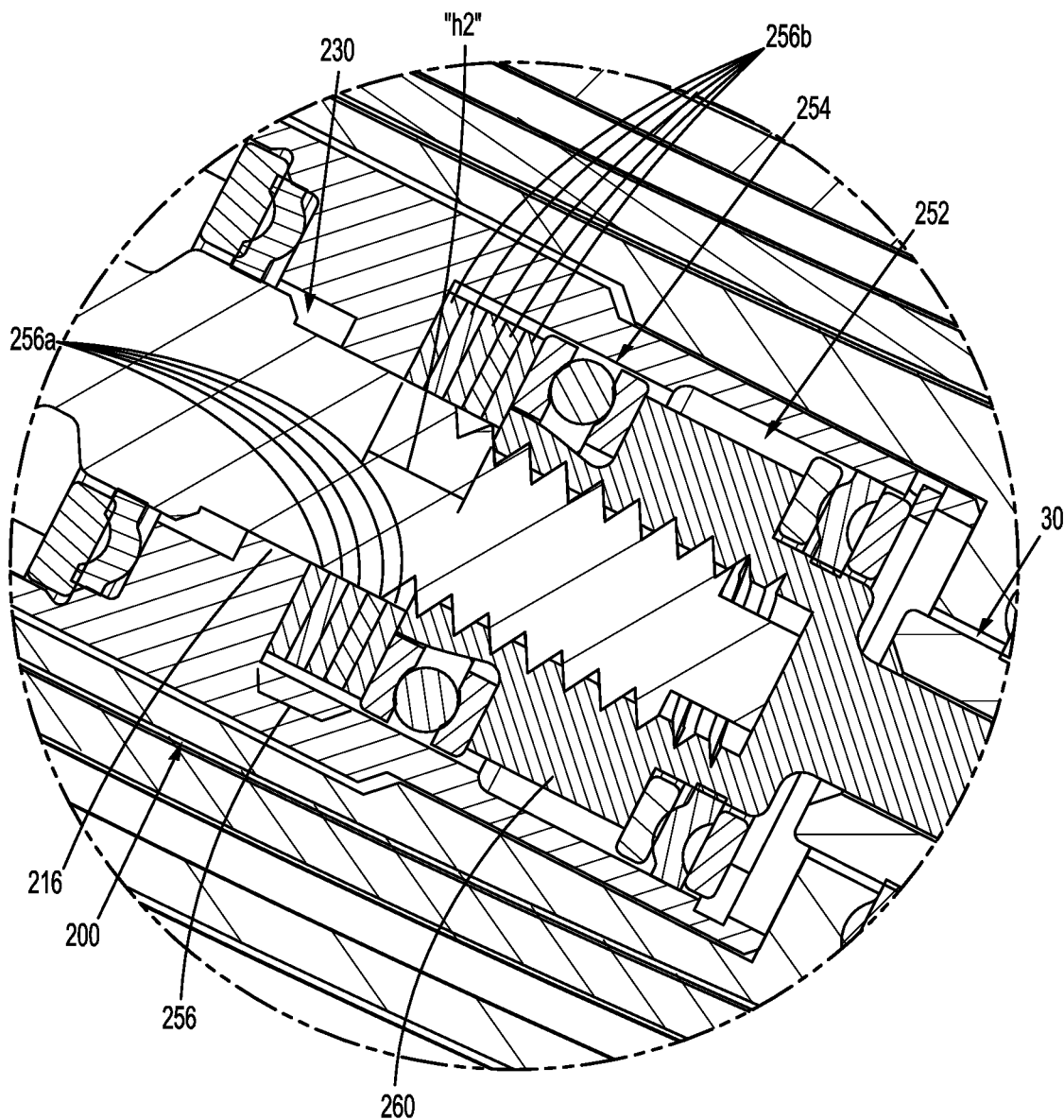
FIG. 17 is an enlarged view of the indicated area of detail shown in FIG. 6.

FIGS. 16 and 17 illustrate the trocar assembly 200, and more particularly, the bearing assembly 250, during stapling and/or cutting of tissue (not shown). During tissue stapling and/or cutting, the drive member 230 remains stationary. The increase axial load experienced by the drive member 230 during tissue stapling and/or cutting causes the plurality of Belleville washers 256 to deform to the second configuration having the second height "h2". In this manner, the axial load experienced by the drive member 230 is shared with the extension portion 264 of the base member 252. More particularly, deforming or flattening of the plurality of Belleville washers 256 to the second configuration causes the inner portions 256a of the plurality of Belleville washers 256 to engage the extension portion 264 of the base member 252. As such, the additional axial load experienced by the drive member 230 during tissue stapling and/or cutting is at least partially diverted from the thrust bearing 254 to prevent damage to the thrust bearing 254 during tissue stapling and/or cutting.

Subsequent to stapling and/or cutting tissue, the increased load experienced by the drive member 230 dissipates, and the plurality of Belleville washers 256 are allowed to return to their first configuration. As the plurality of Belleville washers 256 resume their conical form, the inner portion 256a of the plurality of Belleville washer 256 disengage from the extension portion 264 of the base member 252 of the bearing assembly 250 such that the axial load experienced by the drive member 230 is once again transferred solely through the thrust bearing 254 of the bearing assembly 250.

Although the illustrative aspects of the disclosure have been described herein with reference to the accompanying drawings, it is to be understood that the disclosure is not limited to those precise aspects, and that various other changes and modifications may be affected therein by one skilled in the art without departing from the scope or spirit of the disclosure.

What is claimed is:

1. A trocar assembly for a surgical stapling instrument, the trocar assembly comprising:

a housing including a tubular body having a proximal portion and a distal portion, the housing including a flange;

a trocar member slidably supported within the housing and movable between a retracted position and an advanced position;

a drive member in operable engagement with the trocar member to cause longitudinal movement of the trocar member relative to the housing between the advanced position and the retracted position, the drive member including a flange;

a bearing assembly disposed within the housing between the flange of the housing and the flange of the drive member, the bearing assembly configured to rotatably support the drive member and including a thrust bearing, a rigid member, and a compressible member disposed between the thrust bearing and the rigid member, wherein the compressible member includes a first compressed condition having a first thickness during a clamping stroke of the surgical stapling instrument and a second compressed condition having a second thickness during a stapling stroke of the surgical stapling instrument, the second thickness being less than the first thickness.

2. The trocar assembly of claim 1, wherein the rigid member is spaced from the flange of the drive member during the clamping stroke of the surgical stapling instrument.

3. The trocar assembly of claim 2, wherein the rigid member is in engagement with the flange of the drive member during the stapling stroke of the surgical stapling instrument.

4. The trocar assembly of claim 1, wherein the compressible member includes an uncompressed condition.

5. The trocar assembly of claim 4, wherein the rigid member is spaced from the flange of the drive member prior to the clamping stroke of the surgical stapling instrument.

6. The trocar assembly of claim 4, wherein the compressible member transitions from the uncompressed condition to the first compressed condition as the trocar member moves from the advanced position to the retracted position.

7. The trocar assembly of claim 1, wherein the rigid member includes a proximal annular portion and a distal annular portion, the distal annular portion being larger than the proximal annular portion.

8. The trocar assembly of claim 7, wherein the thrust bearing and soft member are annular.

9. The trocar assembly of claim 8, wherein the thrust bearing and soft member are received about the proximal annular portion of the rigid member.

10. A trocar assembly for a surgical stapling instrument, the trocar assembly comprising:
a housing including a tubular body having a proximal portion and a distal portion, the housing including a flange;
a trocar member slidably supported within the housing and movable between a retracted position and an advanced position;
a drive member in operable engagement with the trocar member to cause longitudinal movement of the trocar member relative to the housing between the advanced position and the retracted position, the drive member including a flange;
a bearing assembly disposed within the housing between the flange of the housing and the flange of the drive member, the bearing assembly configured to rotatably support the drive member and including a thrust bearing, a rigid member, and a compressible member disposed between the thrust bearing and the rigid member, wherein the rigid member is spaced from the flange of the drive member during a clamping stroke of the surgical stapling instrument and the rigid member engages the flange of the drive member during a stapling stroke of the surgical stapling instrument.

11. The trocar assembly of claim 10, wherein the compressible member includes a first compressed condition having a first thickness during the clamping stroke of the surgical stapling instrument and a second compressed condition having a second thickness during the stapling stroke of the surgical stapling instrument, the second thickness being less than the first thickness.

12. The trocar assembly of claim 11, wherein the compressible member includes an uncompressed condition.

13. The trocar assembly of claim 12, wherein the compressible member transitions from the uncompressed condition to the first compressed condition as the trocar member moves from the advanced position to the retraction position.

14. The trocar assembly of claim 10, wherein the rigid member includes a proximal annular portion and a distal annular portion, the distal annular portion being larger than the proximal annular portion.

15. The trocar assembly of claim 14, wherein the thrust bearing and soft member are annular.

16. The trocar assembly of claim 15, wherein the thrust bearing and soft member are received about the proximal annular portion of the rigid member.

17. A surgical stapling instrument having a clamping stroke and a stapling stroke, the surgical stapling instrument comprising:
an adapter assembly; and
a trocar assembly disposed within the adapter assembly, the trocar assembly including,
a housing including a tubular body having a proximal portion and a distal portion, the housing including a flange;
a trocar member slidably supported within the housing and movable between a retracted position and an advanced position;
a drive member in operable engagement with the trocar member to cause longitudinal movement of the trocar member relative to the housing between the advanced position and the retracted position, the drive member including a flange;
a bearing assembly disposed within the housing between the flange of the housing and the flange of the drive member, the bearing assembly configured to rotatably support the drive member and including a thrust bearing, a rigid member, and a compressible member disposed between the thrust bearing and the rigid member, wherein the rigid member is spaced from the flange of the drive member during the clamping stroke and engages the flange of the drive member during the stapling stroke.

18. The surgical stapling instrument of claim 17, wherein the trocar assembly is releasable from the adapter assembly.

19. The surgical stapling instrument of claim 17, further including a handle assembly, the adapter assembly being releasably securable to the handle assembly.

20. The surgical stapling instrument of claim 17, further including an anvil assembly supported on the trocar member.

* * * * *